(12) United States Patent
Sheikh

(10) Patent No.: US 9,650,179 B2
(45) Date of Patent: May 16, 2017

(54) CAP WITH OVERMOLDED GASKET ANCHORING SYSTEM

(71) Applicant: Shahid Sheikh, Santa Monica, CA (US)

(72) Inventor: Shahid Sheikh, Santa Monica, CA (US)

(73) Assignee: PROSERIES LLC, Santa Monica, CA (US)

( * ) Notice: Subject to any disclaimer, the term of this patent is extended or adjusted under 35 U.S.C. 154(b) by 33 days.

(21) Appl. No.: 14/308,755

(22) Filed: Jun. 19, 2014

(65) Prior Publication Data

US 2015/0016755 A1  Jan. 15, 2015

Related U.S. Application Data

(63) Continuation-in-part of application No. 13/327,636, filed on Dec. 15, 2011.

(51) Int. Cl.
*B65D 39/16* (2006.01)
*B65D 41/00* (2006.01)
(Continued)

(52) U.S. Cl.
CPC ............ *B65D 33/16* (2013.01); *A61F 7/103* (2013.01); *B29D 99/0096* (2013.01); *B65D 39/088* (2013.01); *B65D 51/1683* (2013.01); *A61F 2007/105* (2013.01); *B29C 45/14344* (2013.01); *B29C 45/1676* (2013.01); *B29C 66/304* (2013.01); *B29L 2031/565* (2013.01);
(Continued)

(58) Field of Classification Search
CPC .. B65D 41/045; B65D 41/0435; B65D 41/30; B65D 41/0485; B65D 2251/02; B65D 41/0421; B65D 41/0407; B65D 41/065; B29C 66/304; B29C 45/1676; B29C 45/14344; B29C 37/0085; B29L 2031/565; B29L 2031/56; A61F 7/08; A61F 7/10
USPC ........ 220/304; 215/341, 270, 343, 252, 317, 215/329, 295, 305, 334; 383/901; 216/39; 264/273, 247, 274, 275, 268, 264/322, 40.4, 148
See application file for complete search history.

(56) References Cited

U.S. PATENT DOCUMENTS 809,141 A * 1/1906 Schutz .................... A61F 7/086
383/36
1,410,237 A * 3/1922 Baldwin ................ B65D 39/08
220/304
(Continued)

FOREIGN PATENT DOCUMENTS

IT  WO2006134621  * 12/2006  ......... B65D 39/0064

OTHER PUBLICATIONS

International Search Report and Written Opinion from International Patent Appl. No. PCT/US2012/069394, mailed Feb. 20, 2013, in 9 pages.
(Continued)

*Primary Examiner* — J. Gregory Pickett
*Assistant Examiner* — Gideon Weinerth

(57) ABSTRACT

An ice bag is described having a bladder formed with an opening, a threaded receiver coupled to the bladder at the opening, a threaded cap having a first portion formed of a rigid material and a second portion formed of an overmold material, the second portion providing a seal between the receiver and cap with the cap threaded into the receiver.

18 Claims, 14 Drawing Sheets

(51) Int. Cl.
*B65D 33/16* (2006.01)
*A61F 7/10* (2006.01)
*B29D 99/00* (2010.01)
*B65D 39/08* (2006.01)
*B65D 51/16* (2006.01)
*B65D 41/04* (2006.01)
*B29L 31/56* (2006.01)
*B29C 45/16* (2006.01)
*B29C 45/14* (2006.01)
*B29C 65/00* (2006.01)

(52) U.S. Cl.
CPC .. *B31B 2219/9054* (2013.01); *B65D 41/0407* (2013.01); *B65D 2251/02* (2013.01); *B65D 2539/006* (2013.01)

(56) References Cited

U.S. PATENT DOCUMENTS

| | | | | |
|---|---|---|---|---|
| 1,520,812 A * | 12/1924 | Eggers | B65D 41/0492 | 383/60 |
| 1,548,276 A * | 8/1925 | Mulloy | B65D 51/1683 | 137/533.17 |
| 1,640,430 A * | 8/1927 | Stanley | A61F 7/086 | 220/288 |
| 1,738,612 A * | 12/1929 | Recht | B21D 51/46 | 264/268 |
| 1,754,776 A * | 4/1930 | Stanley | B65D 39/08 | 220/304 |
| 1,834,978 A * | 12/1931 | Shapiro | A61F 7/103 | 383/120 |
| 1,956,012 A * | 4/1934 | Egan | B21D 51/46 | 215/349 |
| 2,068,389 A * | 1/1937 | Smith | B65D 41/045 | 215/350 |
| 2,215,392 A * | 9/1940 | Freeman | B65D 41/225 | 215/307 |
| 2,289,887 A * | 7/1942 | Shapiro | A61F 7/103 | 220/304 |
| 2,663,910 A * | 12/1953 | Danielson | B29C 45/16 | 235/1 C |
| 2,849,141 A * | 8/1958 | Abbiati | B65D 41/0435 | 215/228 |
| 3,095,104 A | 6/1963 | Stover | | |
| 3,189,209 A * | 6/1965 | Owens | B65D 41/045 | 215/329 |
| 3,306,327 A | 2/1967 | Ilg | | |
| 3,458,077 A * | 7/1969 | Ryan | B65D 41/045 | 215/329 |
| 3,473,683 A * | 10/1969 | Zipper | B29C 70/80 | 215/345 |
| 3,739,938 A | 6/1973 | Paz | | |
| 3,750,822 A | 8/1973 | Dubach | | |
| 3,883,025 A * | 5/1975 | Jemmett | B29C 70/80 | 215/341 |
| 4,308,965 A * | 1/1982 | Dutt | B65D 41/0442 | 215/345 |
| 4,331,249 A * | 5/1982 | Banich, Sr. | B65D 41/0442 | 215/343 |
| 4,343,754 A * | 8/1982 | Wilde | B29C 37/0082 | 264/154 |
| 4,378,893 A * | 4/1983 | Wilde | B65D 41/0435 | 215/246 |
| 4,440,820 A * | 4/1984 | Shiho | B29C 45/16 | 264/245 |
| 4,461,393 A * | 7/1984 | Dutt | B65D 41/0442 | 215/329 |
| 4,489,844 A * | 12/1984 | Breskin | B65D 41/0442 | 215/329 |
| 4,527,705 A * | 7/1985 | Prades | B65D 41/3447 | 215/252 |
| 4,545,499 A * | 10/1985 | Bennett | B65D 41/0442 | 215/352 |
| 4,697,716 A * | 10/1987 | Mumford | B65D 41/0442 | 215/341 |
| 4,938,371 A * | 7/1990 | Vercillo | B65D 53/06 | 215/352 |
| 5,090,409 A | 2/1992 | Genis | | |
| 5,443,172 A * | 8/1995 | Gabriele | B65D 41/0485 | 215/295 |
| 5,686,040 A * | 11/1997 | Taber | B29C 31/047 | 264/268 |
| 5,688,461 A * | 11/1997 | Howie, Jr. | B29C 45/1676 | 264/271.1 |
| 5,769,255 A * | 6/1998 | Ohmi | B29C 70/80 | 215/341 |
| 5,853,097 A * | 12/1998 | Ekkert | B65D 41/3447 | 215/252 |
| 5,868,273 A | 2/1999 | Daenen | | |
| 5,941,404 A * | 8/1999 | Charrette | B65D 41/04 | 215/305 |
| 6,142,325 A * | 11/2000 | Chomik | A61J 9/04 | 215/341 |
| 6,202,872 B1 * | 3/2001 | Smeyak | B65D 41/045 | 215/343 |
| 6,248,280 B1 * | 6/2001 | Kern | B01D 46/0001 | 264/263 |
| 6,306,330 B1 * | 10/2001 | Cerny | B29C 43/146 | 264/255 |
| 6,589,272 B1 * | 7/2003 | Sheikh | A61F 7/02 | 607/108 |
| 6,627,135 B1 * | 9/2003 | Chomik | A61J 9/04 | 264/250 |
| 6,702,133 B1 * | 3/2004 | Shenkar | B65D 41/045 | 215/249 |
| 6,712,365 B2 * | 3/2004 | Baringa | B41J 2/17596 | 220/359.3 |
| 6,805,207 B2 | 10/2004 | Hagan | | |
| 7,007,817 B2 | 3/2006 | Jochem | | |
| 7,073,678 B1 | 7/2006 | Dibdin | | |
| 7,097,790 B2 | 8/2006 | Jochem | | |
| 7,431,976 B2 * | 10/2008 | Hermann | A44B 18/0076 | 24/442 |
| 7,802,690 B2 * | 9/2010 | Lohrman | B65D 41/0485 | 215/252 |
| 7,841,489 B2 | 11/2010 | Gilbertson | | |
| 7,887,731 B2 | 2/2011 | Schmeisser | | |
| 8,109,396 B1 * | 2/2012 | Robinson | B65D 41/0485 | 215/220 |
| D711,227 S * | 8/2014 | Sheikh | D9/435 | |
| 8,881,929 B2 * | 11/2014 | Ekkert | B65D 43/0231 | 215/232 |
| 2001/0019055 A1 * | 9/2001 | Gaster | B29C 45/14614 | 220/4.21 |
| 2002/0113032 A1 | 8/2002 | Blomdahl | | |
| 2003/0098286 A1 | 5/2003 | Bloom | | |
| 2003/0098287 A1 * | 5/2003 | Taber | B29C 45/0025 | 215/352 |
| 2004/0011759 A1 * | 1/2004 | Hahn | B29C 45/1676 | 215/305 |
| 2004/0060894 A1 * | 4/2004 | Parrinello | B29C 43/146 | 215/347 |
| 2004/0245207 A1 | 12/2004 | Chomik | | |
| 2004/0256393 A1 * | 12/2004 | Van De Klippe | B65D 39/084 | 220/304 |
| 2005/0061766 A1 | 3/2005 | Jochem | | |
| 2005/0062183 A1 * | 3/2005 | Jochem | B29C 37/0085 | 264/40.4 |
| 2007/0292054 A1 * | 12/2007 | Chang | A61F 7/08 | 383/80 |
| 2008/0073312 A1 * | 3/2008 | Babcock | B65D 41/0485 | 215/305 |
| 2008/0111276 A1 * | 5/2008 | Hahn | B29C 45/1676 | 264/268 |
| 2008/0251492 A1 | 10/2008 | Shi | | |
| 2010/0133275 A1 * | 6/2010 | Phillips | B65D 7/40 | 220/270 |
| 2011/0133376 A1 * | 6/2011 | Hackett | B29C 45/0001 | 267/145 |

(56) References Cited

U.S. PATENT DOCUMENTS

| | | | |
|---|---|---|---|
| 2012/0031142 A1 | 2/2012 | Marton | |
| 2012/0234791 A1* | 9/2012 | Weber | B29C 37/0082 216/39 |
| 2012/0312816 A1* | 12/2012 | Barreto | B65D 43/022 220/254.7 |
| 2013/0158637 A1* | 6/2013 | Sheikh | B31B 1/00 607/114 |
| 2015/0056089 A1* | 2/2015 | Gledhill, III | F16J 3/02 417/472 |
| 2015/0102032 A1* | 4/2015 | Dunn | A47G 19/2272 220/231 |

OTHER PUBLICATIONS

International Search Report and Written Opinion from International Patent Appl. No. PCT/US15/35761, mailed Sep. 11, 2015, in 16 pages.

* cited by examiner

CAP WITH OVERMOLDED GASKET ANCHORING SYSTEM

This application is a continuation-in-part application of U.S. patent application Ser. No. 13/327,636 filed Dec. 15, 2011, titled "Ice Bag Closures and Methods for Manufacturing Ice Bag Closures". The entire contents of U.S. patent application Ser. No. 13/327,636 are hereby incorporated by reference herein. This application is also related to PCT Patent Application No. PCT/US2012/069394 (WO2013/090514), filed Dec. 13, 2012, titled "Ice Bag Closures and Methods for Manufacturing Ice Bag Closures", the entire contents of which are hereby incorporated by reference herein.

FIELD

The present invention pertains generally to ice bags. More particularly, the present invention pertains to ice bag closures and methods for manufacturing ice bag closures.

BACKGROUND

Ice bags, which are also commonly referred to as medical ice bags or English style ice bags, generally include a bladder that is made of a waterproof material, such as an impervious cloth-like fabric, and is shaped having a relatively wide mouth or opening allowing ice cubes to be passed through the opening and into the bladder. A closure assembly is typically provided to open, close and seal the bladder opening. For example, the closure assembly may include a receiver that is fastened or clamped to the bladder material and a screw cap that threads into the receiver.

To use the ice bag, the screw cap may be removed to fill the bladder with ice, ice water, chilled or heated water or other thermal mixtures or solutions at a selected temperature. Once filled, the cap is replaced and the ice bag can be applied to a portion of the user's body. For example, the ice bag may be manually applied and held against a portion of the user's body or a wrap may be used to press and secure the ice bag against a portion of the user's body. In this regard, U.S. Pat. No. 6,589,272 granted on Jul. 8, 2003 to Sheikh and titled "Thermal Pack Retaining Apparatus" discloses a joint-specific apparatus that reliably retains a cold pack in a preselected position and under compression adjacent to an anatomical structure such as a limb or joint, the entire contents of U.S. Pat. No. 6,589,272 are hereby incorporated by reference herein.

Ice bags can be used to reduce pain, swelling and inflammation, for example, during rehabilitation of injured joints and muscles and in post-surgical patients. For example, joints may be injured during exercise, while engaging in sporting or on-the-job activities or during an accident such as a fall. These injuries can include circumstances in which a muscle, ligament or tendon is sprained, torn or otherwise traumatized.

In the past, a removable gasket has been used to create a water-tight seal between the screw cap and receiver of an ice bag. However, the removable gasket is often lost or damaged rendering the ice bag unusable. In addition, the small gasket, if removed from the cap, can present a choke hazard for small children and infants. Moreover, debris which enters the gap between the gasket and cap can cause the closure assembly to leak.

In light of the above, Applicant discloses Ice Bag Closures and Methods for Manufacturing Ice Bag Closures.

SUMMARY

In one aspect of the present disclosure, an ice bag is described herein which comprises; a bladder formed with an opening; a threaded receiver coupled to the bladder at the opening; a threaded cap having a first portion formed of a rigid material and a second portion formed of an overmold material, the second portion providing a seal between the receiver and cap with the cap threaded into the receiver.

In one embodiment of this aspect, the receiver has a first portion formed of a rigid material and a second portion formed of an overmold material, the second portion providing a seal between the receiver and bladder with the bladder coupled to the receiver.

In one arrangement of this aspect, the first portion of the cap comprises a hollow cylindrical portion and a flange and wherein the overmold material overlays a surface of the flange.

In one setup of this aspect, the flange surface is formed with a recess to increase bond strength between the overmold material and the flange.

In one implementation of this aspect, the flange extends to lip formed with a plurality of cutouts and the overmold material overlays a surface of the lip and establishes a plurality of grips for the cap within the cutouts.

In a particular embodiment of this aspect, the overmold material is a thermoplastic elastomer.

In one arrangement of this aspect, the rigid material is a plastic.

In another aspect, an ice bag is described herein which comprises; a first threaded component and a second component, the first component having a first portion formed of a rigid material and a second portion formed of an elastomer fixedly attached to the first portion to provide a seal between the first and second components when the first and second components are coupled together.

In one embodiment of this aspect, the first threaded component is a receiver and the second component is a bladder.

In one embodiment of this aspect, the first threaded component is a receiver and the second component is a cap.

In one implementation of this aspect, the first threaded component is a cap and the second component is a receiver.

In a particular implementation of this aspect, the elastomer is fixedly attached to the first portion using an adhesive.

In a particular embodiment of this aspect, the elastomer is an overmold material.

In one arrangement of this aspect, the second component has a first portion formed of a rigid material and a second portion formed of an elastomer fixedly attached to the first portion of the second component to provide a seal between the second component and a third component when the second and third components are coupled together.

In another aspect, a method of producing an ice bag is described herein comprising the steps or acts of; providing a bladder formed with an opening; molding a first threaded component formed of a rigid material and a second component formed of a rigid material; and overlying a thermoplastic elastomer material on a portion of the first threaded component in an overmolding process to produce a seal.

In one embodiment of this aspect, the overmolding process is a multi-shot injection molding process.

In one implementation of this aspect, the overmolding process is an insert molding processes.

In one implementation of this aspect, the first threaded component is a cap.

In a particular implementation of this aspect, the first threaded component is a receiver.

In a particular embodiment of this aspect, the step of overlying a thermoplastic elastomer material overlays a thermoplastic elastomer material on a receiver flange to produce a seal between the receiver and a cap.

In another aspect of the present disclosure, an ice bag is described herein which comprises; a bladder formed with an opening; a threaded receiver coupled to the bladder at the opening, the receiver having a first portion formed of a rigid material and a second portion formed of an overmold material, the second portion providing a seal between the receiver and bladder with the bladder coupled to the receiver; and a threaded cap.

In another aspect, an ice bag is described herein made by the process comprising the steps or acts of; providing a bladder formed with an opening; molding a first threaded component formed of a rigid material and a second component formed of a rigid material; and overlying a thermoplastic elastomer material on a portion of the first threaded component in an overmolding process to produce a seal.

In yet another aspect, an ice bag is described herein that includes an integral valve comprising a chamber having a first end and a second end, the chamber having a moveable button at the first chamber end and formed with a plurality of openings at the second chamber end with the button formed with a plurality of holes. For this aspect, a valve stem is affixed to the button and has an overmolded seal formed thereon, the valve stem moveable with the button to reconfigure the valve between a first closed configuration in which the seal covers the openings and a second open configuration in which air can flow into the openings, through the chamber and out through the holes to release air from an ice bag. In one embodiment of this aspect, the overmolded seal is made of a thermoplastic elastomer. In a particular embodiment, the holes have a substantially same size as the openings and there are more holes in the button than openings at the second chamber end. In one embodiment, the ice bag cap comprises two holes and four openings. The ice bag cap can include a spring to bias the valve stem into the closed configuration in which the seal covers the openings.

In still another aspect, a cap includes a first portion formed of a rigid material, the first portion formed with a through-hole; and a second portion formed of an overmold material, the second portion extending through the though-hole and establishing a seal on a first side of the though-hole and establishing a mechanical anchor for the seal on a second side of the through-hole. In one embodiment, the first portion is threaded. In a particular embodiment, the first portion of the cap comprises a hollow cylindrical portion and a flange and the through-hole is formed in the flange.

In a particular embodiment of this aspect, the overmold material overlays a surface of the flange to establish the seal. In one embodiment, the overmold material overlays a surface of the flange to establish the mechanical anchor for the seal. For all of these embodiments, the through-hole can be a plurality of through-holes. In one embodiment, the overmold material is a thermoplastic elastomer. In a particular embodiment, the rigid material is a plastic.

In another aspect, a threaded cap for covering an opening of a container and providing a seal between the cap and the container includes a rigid portion having a threaded cylinder and a flange. For example, the container can be an ice bag, water bottle or some other container known in the pertinent art that requires closure by a threaded, resealable cap. For the cap, the flange extends from the threaded cylinder, e.g. outwardly, and is formed with a through-hole. Also, an elastomeric portion extends through the though-hole and overlays at least a portion of a first surface of the flange and at least a portion of an opposed, second surface of the flange. In one embodiment, the elastomeric portion overlays the first surface of the flange establishing a seal and the elastomeric portion overlays the second surface of the flange establishing a grip for the cap. In one particular embodiment, the elastomeric portion overlays the first surface of the flange establishing a seal and the elastomeric portion overlays the second surface of the flange establishing a mechanical anchor for the seal.

In another aspect, a method for producing a cap comprises the steps of molding a first threaded component formed of a rigid material, the first threaded component formed with a through-hole; and overmolding a thermoplastic elastomer material on the first threaded component, the thermoplastic elastomer material extending through the though-hole and establishing a seal on a first side of the though-hole and establishing a mechanical anchor for the seal on a second side of the through-hole. In one implementation of this method, the overmolding step is accomplished using a multi-shot injection molding process. In another implementation of this method, the overmolding step is accomplished using an insert molding processes. In one particular implementation, the first threaded component is formed with a plurality of through-holes.

DETAILED DESCRIPTION

Figure 1:
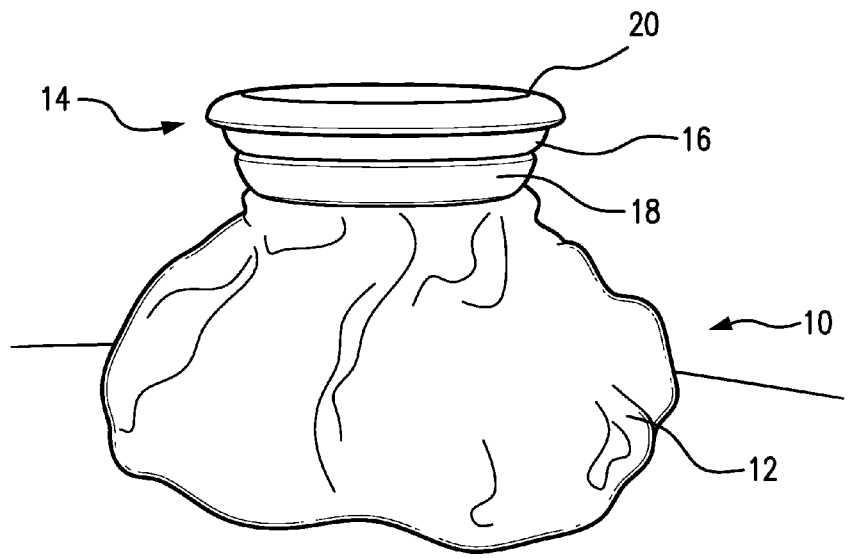
FIG. 1 shows a perspective view of an ice bag.

Referring to FIG. 1, an ice bag for holding a material contents at a selected temperature and applying the material contents to a portion of a person's anatomy to facilitate a thermal exchange between the material contents and the portion of a person's anatomy is shown and generally designated 10.

As shown in FIG. 1, the ice bag 10 includes a bladder 12 that is shaped to envelop a volume suitable for holding a material contents such as ice. The bladder 12 is generally formed of a water impervious material such as an elastomeric material or a cloth that has been coated with a water impervious coating. As shown, the bladder forms an opening allowing fluids and solids such as ice to be delivered into and removed from the bladder 12. The bladder may be pre-formed, e.g. heat molded, into the desired shape or, as shown, may be formed of a sheet, the edges of which are gathered together and pleated to form the opening.

As detailed further below, FIG. 1 shows that the ice bag 10 includes a closure 14 at the opening of the bladder 12 to close and prevent the contents in the bladder 12 from leaking. As shown, the closure 14 includes a receiver 16 that is affixed to the bladder opening, e.g. pleats, using a clamp ring 18 that can sandwich the pleated fabric between the clamp ring 18 and receiver 16, for example, using a swaging or clamping technique. Alternative techniques for attaching the bladder to the receiver may be used, for example, the receiver may be bonded to the bladder. It can be further seen in FIG. 1 that the closure 14 includes a removable cap 20 that is threaded into the receiver 16.

Figure 2:
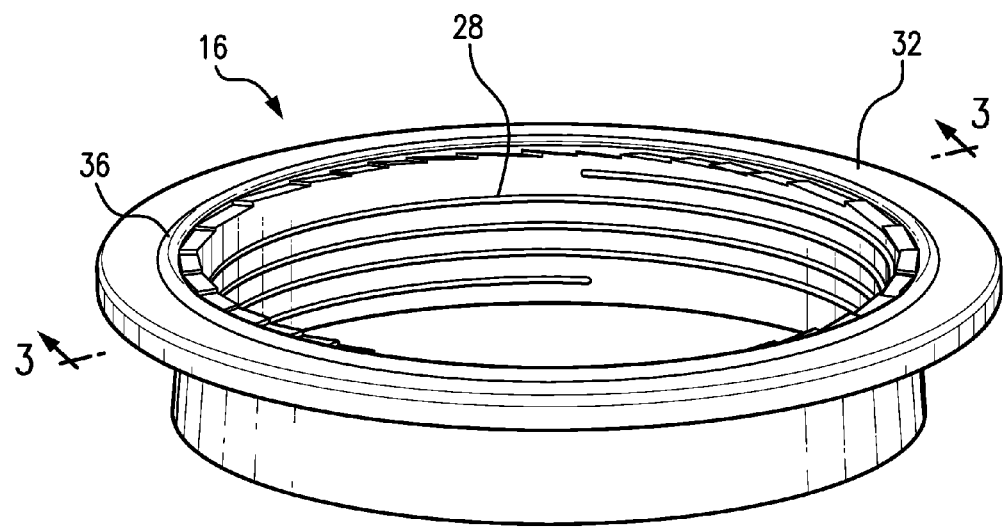
FIG. 2 shows a perspective view of a receiver for use in the ice bag shown in FIG. 1.
Figure 3:
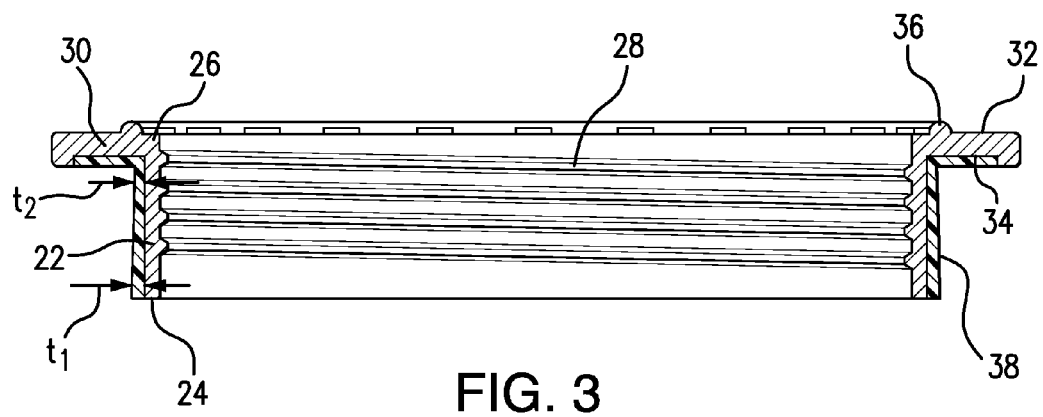
FIG. 3 shows a sectional view of the receiver shown in FIG. 2 as seen along line 3-3 in FIG. 2.

FIGS. 2 and 3 show an embodiment of a receiver 16 for use in the ice bag 10 shown in FIG. 1. As seen there, the receiver 16 can include a hollow cylindrical portion 22 that extends from a first end 24 to a second end 26. One or more thread features 28 extend from the inner wall of the cylindrical portion 22 to establish a set of internal, female threads for the receiver 16. For example, the cylindrical portion may have an internal cylinder diameter of about 1.5 to 3 inches (38-76 mm). Receiver 16 includes an annular flange 30 that extends outwardly from cylinder portion 22 at second end 26 and establishes a first flange surface 32 and opposed second flange surface 34. Raised protrusion 36 having a rounded profile is formed on surface 32 and extends, unbroken, annularly around the entire length of the first flange surface 32. Cylindrical portion 22, thread features 28, annular flange 30 and raised protrusion 36 can be made of a one-piece rigid material, for example, a molded rigid plastic.

The term "rigid material" as used herein is a broad term, and is to be given its ordinary and customary meaning to a person of ordinary skill in the art (and is not to be limited to a special or customized meaning), and refers without limitation to a material that does not substantially compress, deform or change shape during an ordinary use, and, if applicable, for a plurality of use cycles. Examples of rigid materials include, but are not necessarily limited to metals, wood and plastics including Acetal, Acrylonitrile Butadiene Styrene, Polycarbonate, Polypropylene, Polyethylene, Polystyrene, High Impact Polystyrene, Polymethylmethacrylate, Polyesters, Copolyester, Polyamide, Polybutylene Terephthalate, Polyphenylene Oxide, Glycol Modified Polyethylene Terephthalate and their blends and alloys.

FIGS. 2 and 3 further show that the receiver 16 may include an overmold material overlying the outer surface of cylindrical portion 22 and a portion of the surface 34 of flange 30. As shown, the overmold material may be thicker, "$t_1$" near the first end 24 of the cylindrical portion 22 than near the second end 26, "$t_2$" of the cylindrical portion 22 (i.e. "$t_1$">"$t_2$") to prevent the clamp ring 18 (see FIG. 1) from backing off of the receiver 16 (in use). Typically, the overmold material is a thermoplastic elastomer that is molded onto the rigid plastic cylindrical portion 22 and flange 30 using an overmolding process. For example, the overmold material may have a thickness, "$t_1$" in the range of about 0.3 to 10 mm and a thickness, "$t_2$" in the range of about 0.1 to 5 mm.

During assembly of the ice bag 10 shown in FIG. 1, the first end 24 of the cylindrical portion 22 is inserted into the opening formed in the bladder 12 until the bladder abuts the overmold material overlying the surface 34 of the flange 30. The clamp ring 18 is then installed on the assemble to sandwich and compress the bladder, e.g. pleats and overmold material between the clamp ring 18 and the rigid material portion of the receiver 16, providing a water-tight seal between the receiver 16 and bladder 12.

The term "overmolding" as used herein is a broad term, and is to be given its ordinary and customary meaning to a person of ordinary skill in the art (and is not to be limited to a special or customized meaning), and refers without limitation to a molding process in which an overmold material is molded onto a substrate material and becomes bonded to the substrate material without the use of a third material such as an adhesive. For example, an overmold material consisting of a thermoplastic elastomer (TPE) can be molded onto a rigid substrate. Types of overmolding processes can include, but are not necessarily limited to, multi-shot injection molding processes and insert molding processes. In a multi-shot injection molding process, two (or more) materials, such as a rigid substrate material and overmold material are shot into the same mold during the same molding cycle. In an example of an insert molding process, a pre-molding insert such as a rigid substrate can be placed into a mold and the overmold material can be introduced into the mold where it contacts and adheres to the pre-molded insert.

The term "overmold material" as used herein is a broad term, and is to be given its ordinary and customary meaning to a person of ordinary skill in the art (and is not to be limited to a special or customized meaning), and refers without limitation to a material that is bonded to a substrate material by an overmolding process. Overmold materials include thermoplastic elastomers and other materials that have been bonded to a substrate material by an overmolding process. In some cases, the overmold material may be softer than the substrate material. For example, the overmold material may have a durometer hardness between about 10 shore OO and 80 shore A.

The term "thermoplastic elastomer" as used herein is a broad term, and is to be given its ordinary and customary meaning to a person of ordinary skill in the art (and is not to be limited to a special or customized meaning), and refers without limitation to an elastomeric material that can be applied to a substrate in an overmolding process. Examples of thermoplastic elastomers include, but are not necessarily limited to Copolyamides, Copolyesters, thermoplastic Urethanes, thermoplastic Vulcanizates, Olefinic Copolymers and Styrenic block copolymers. Thermoplastic elastomers having proprietary compositions are often sold under tradenames such as Dynaflex®, Versaflex®, Versollon™, Versalloy® and Noryl®.

The term "elastomer" as used herein is a broad term, and is to be given its ordinary and customary meaning to a person of ordinary skill in the art (and is not to be limited to a special or customized meaning), and refers without limitation to a material that can be deformed, for example, compressed, during ordinary use and subsequently recovers to substantially its original shape when stresses are removed, for a plurality of stress-recovery cycles. Examples of elastomers include, but are not necessarily limited to natural and synthetic rubber including silicone and the thermoplastic elastomers listed above.

Figure 4:
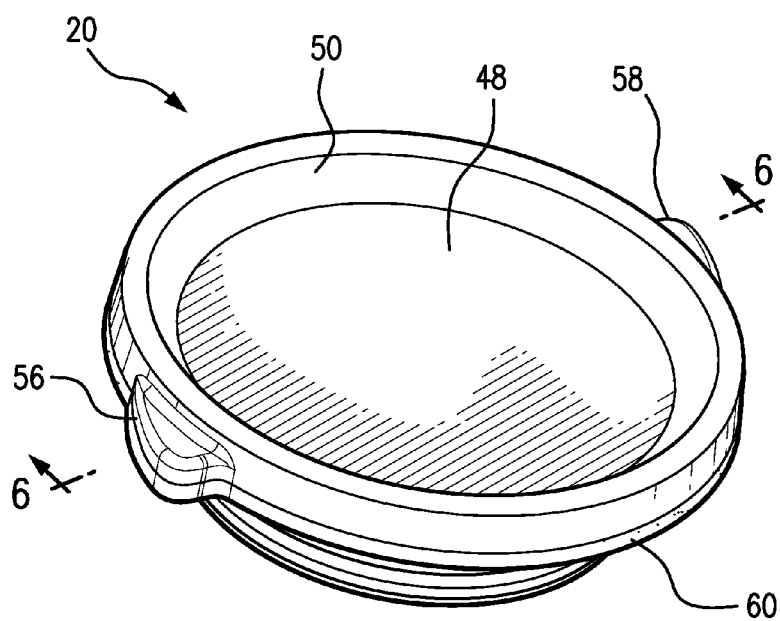
FIG. 4 shows a perspective view of an embodiment of a cap for use in the ice bag shown in FIG. 1.
Figure 5:
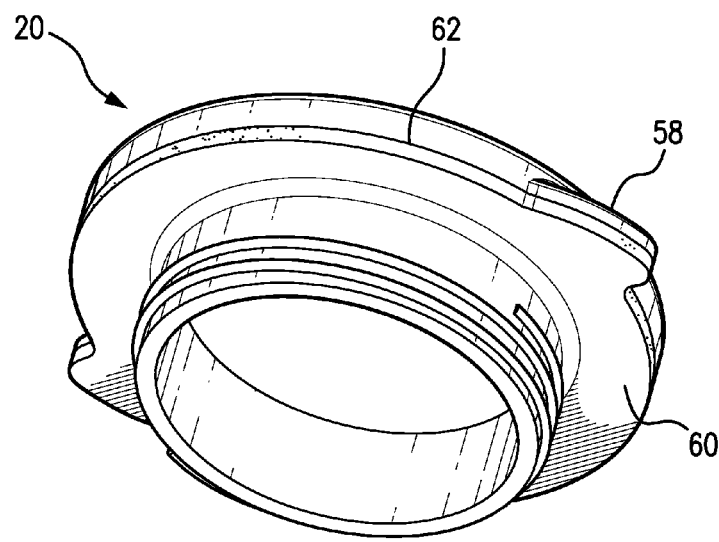
FIG. 5 shows another perspective view of the cap shown in FIG. 4.
Figure 6:
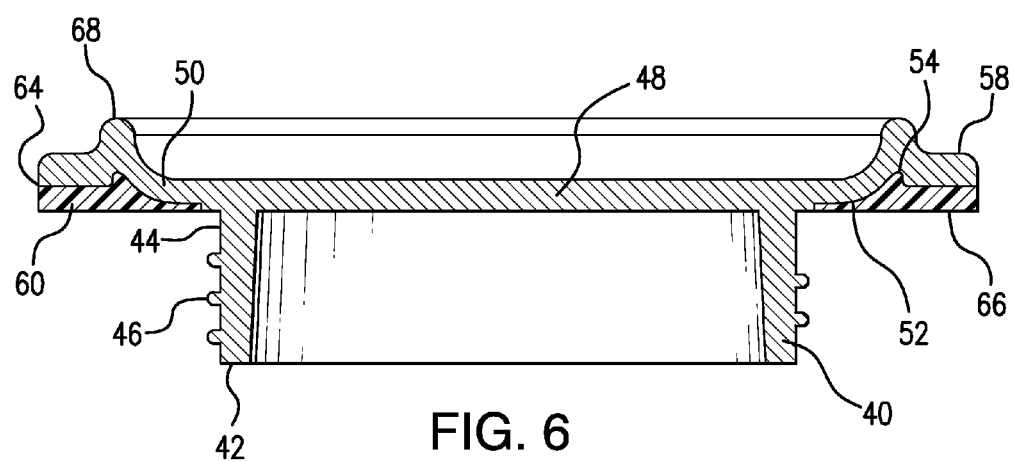
FIG. 6 shows a sectional view of the cap of FIG. 4 as seen along line 6-6 in FIG. 4.

FIGS. 4-6 show an embodiment of a cap 20 for use in the ice bag 10 shown in FIG. 1. As shown, the cap 20 includes a hollow cylindrical portion 40 that extends from a first end 42 to a second end 44. One or more thread features 46 extend from the outer wall of the cylinder portion 40 to establish a set of external, male threads for the cap 20. Cap 20 includes a generally flat cover 48 closing the hollow cylindrical portion 40 at the second end 44. An annular flange 50 that extends outwardly from the cover 48 at second end 44 and establishes a flange surface 52. FIGS. 4 and 6 show that the flange 50 is non-flat and extends away from the cover 48 and out of the plane of the cover 48. FIG. 6 further shows that an annular recess 54 is formed in the flange surface 52 that extends around the entire length of the flange 50. A pair of grips 56, 58 extend from flange 50 to facilitate screwing the cap 20 into the receiver 16 (shown in FIG. 2). Cylindrical portion 40, thread features 46, annular flange 50 and cover 48 can be made of a one-piece rigid material, for example, a molded rigid plastic.

FIGS. 4-6 further show that the cap 20 includes an overmold material 60 overlying the flange surface 52 and extending from the cylindrical portion, into recess 54, and beyond recess 54 to the edge 62 of the flange 50 (and the edge 64 of the grips 56, 58). As shown, the surface 66 of the overmold opposite the flange 50 is substantially flat. Typically, the overmold material is a thermoplastic elastomer that is molded onto the rigid plastic flange 50 and grips 56, 58 using an overmolding process. For example, the overmold material may have a thickness at the edge 62 of the flange 50 in the range of about 0.5 to 15 mm. Recess 54 is provided to increase the bond strength between overmold material 60 and flange 50 (relative to a flat flange) and increase moldability of the rigid material due by providing a flange having a more uniform thickness from the cylindrical portion 40 to the flanged end 68.

The installation of the cap 20 into the receiver 16 can best be appreciated by cross referencing FIGS. 3 and 6. To install, the first end 42 of the cap 20 is inserted in the second end 26 of the receiver 16 to engage thread portions 46 with thread portions 28. The cap is then rotated relative to the receiver (using grips 56, 58) until the overmold 60 contacts the raised protrusion 36. Additional rotation of the cap 20 is then applied until the raised protrusion 36 compresses the overmold material 60 between the raised protrusion 36 and flange 50 to establish a water tight seal between the receiver 16 and cap 20.

Figure 7:
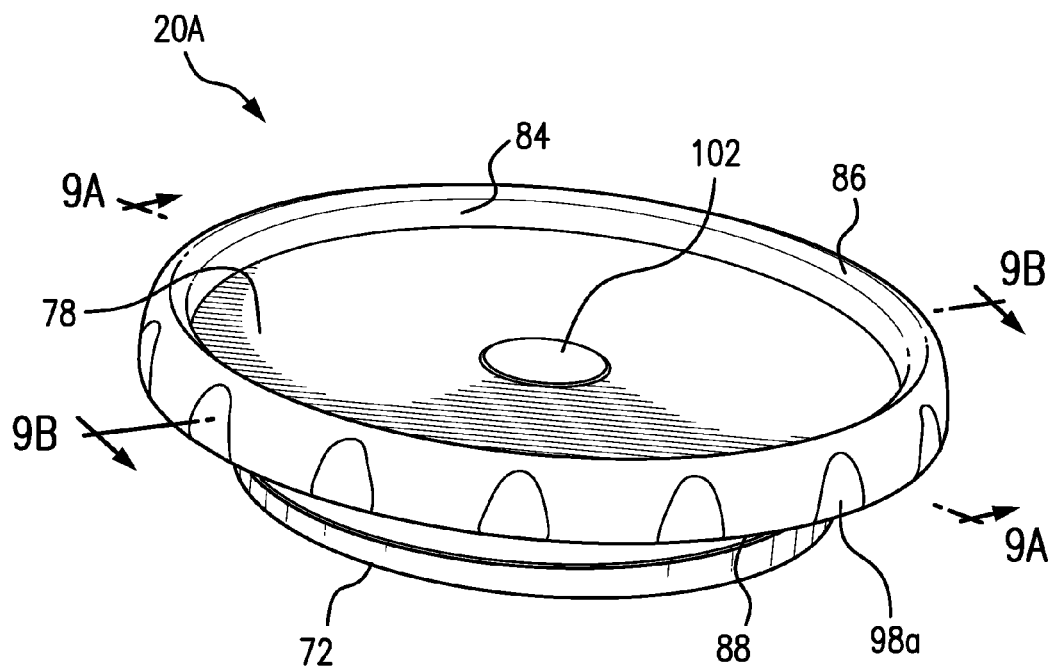
FIG. 7 shows a perspective view of another embodiment of a cap for use in the ice bag shown in FIG. 1.
Figure 8:
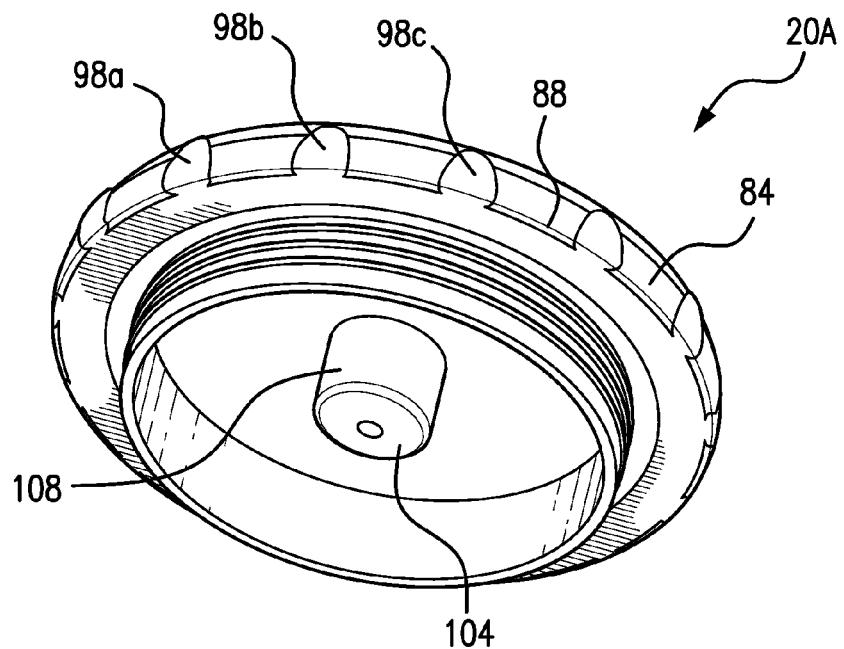
FIG. 8 shows another perspective view of the cap shown in FIG. 7.
Figure 9A:
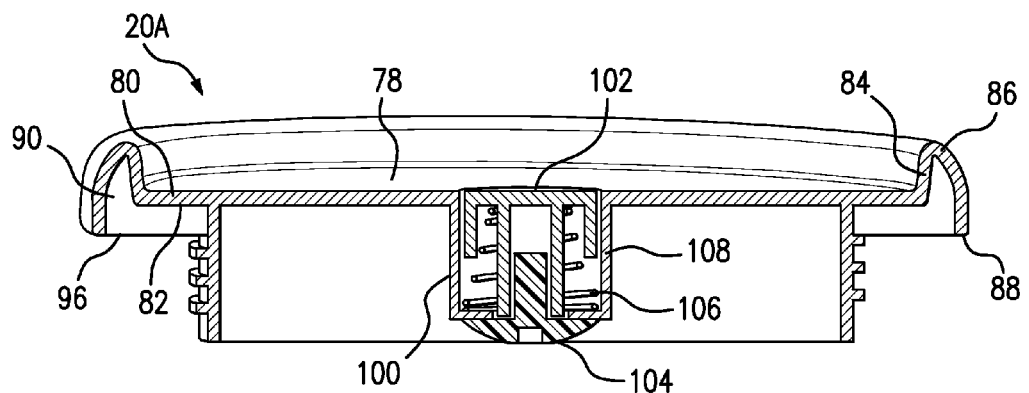
FIG. 9A shows a sectional view of the cap of FIG. 7 as seen along line 9A-9A in FIG. 7 showing a section of the cap in which the lip fully extends to a lip edge.
Figure 9B:
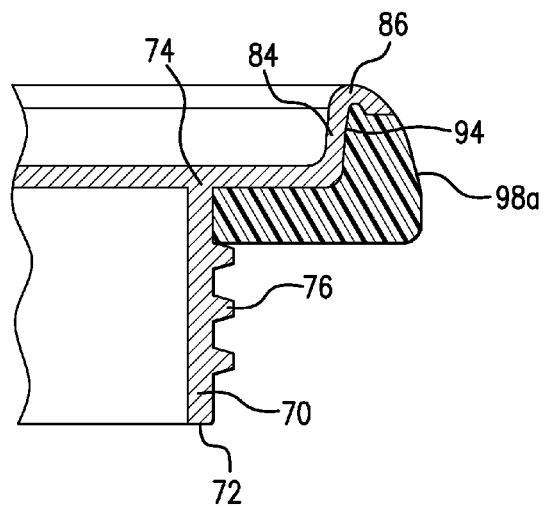
FIG. 9B shows a sectional view of the cap of FIG. 7 as seen along line 9B-9B in FIG. 7 showing a section of the cap in which a cutout is formed in the lip to establish a grip for the cap.

FIGS. 7-9A and 9B show another embodiment of a cap 20A for use in the ice bag 10 shown in FIG. 1. As shown, the cap 20A includes a hollow cylindrical portion 70 that extends from a first end 72 to a second end 74. One or more thread features 76 extend from the outer wall of the cylinder portion 70 to establish a set of external, male threads for the cap 20A. Cap 20A includes a generally flat cover 78 closing the hollow cylindrical portion 70 at the second end 74. An annular flange 80 that extends outwardly from the cover 78 at second end 74 of cylindrical portion 70 and establishes a flange surface 82. FIGS. 9A and 9B show that the flange 80 is substantially flat and extends away from the cover 78 to a lip 84. As shown, lip 84 curls from the flange 80 through an apex 86 to an edge 88. From the apex 86 to the edge 88, the lip is formed with a plurality of cutouts that are spaced around the lip 84. In some embodiments, the cutouts may be equally spaced around the lip 84. Cylindrical portion 70, thread features 76, annular flange 80, lip 84 and cover 78 can be made of a one-piece rigid material, for example, a molded rigid plastic.

FIGS. 7-9 further show that the cap 20A includes an overmold material 90 overlying the flat flange surface 82 and inner surface 94 of curled lip 84. As shown, the surface 96 of the overmold material 90 opposite the flange 80 is substantially flat. Typically, the overmold material is a thermoplastic elastomer that is molded onto the rigid plastic flange 80 and lip 84 using an overmolding process. For example, the overmold material may have a thickness on the flange 80 in the range of about 0.5 to 25 mm. FIGS. 7, 8 and 9A show that the overmold material 90 extends to the edge 88 of the lip 84 to create a plurality of grips (of which grips 98a-c are labeled). The overmold material can be formed to create grips 98a-c that are flush with or slightly raised above the surface of the lip 84.

FIGS. 7-9 also illustrate that a valve 100 may be incorporated into the cap 20A (or any of the other caps 20, 20B, 20C, 20D, 20E, 20F, 20G or 20H described herein). Alternatively, cap 20A may be configured without valve 100 in which case the cover 78 would be continuous like the cover 48 shown in FIG. 4. As shown in FIGS. 7-9A, the valve 100 can include a button 102 that is manually depressible to release air from the bladder 12 (shown in FIG. 1) when the bladder is partially collapsed. As best seen in FIG. 9A, the valve 100 includes a valve-stem 104 that is biased in a closed position (shown closed in FIG. 9A) by spring 106 to cover an opening in chamber 108. Depressing button 102 moves stem 104 to allow air from the bladder to escape through the valve 100.

The installation of the cap 20A into the receiver 16 can best be appreciated by cross-referencing FIGS. 3 and 9A. To install, the first end 72 of the cap 20A is inserted in the second end 26 of the receiver 16 to engage thread portions 76 with thread portions 28. The cap is then rotated relative to the receiver (using grips 98a-c) until the overmold material 90 contacts the raised protrusion 36. Additional rotation of the cap 20A can then applied until the raised protrusion 36 compresses the overmold material 90 between the raised protrusion 36 and flange 80 to establish a watertight seal between the receiver 16 and cap 20A. Once sealed, the button 102 can be depressed and the bladder 12 collapsed to devoid the bladder 12 of air. Removing air from the bladder 12 can improve the ability of the user to conform the ice bag 10 to the targeted anatomical region.

Figure 10:
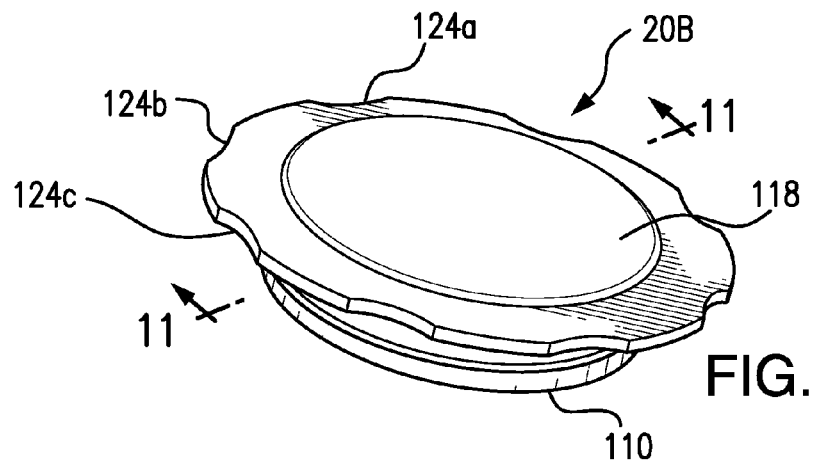
FIG. 10 shows a perspective view of another embodiment of a cap for use in the ice bag shown in FIG. 1.
Figure 11:
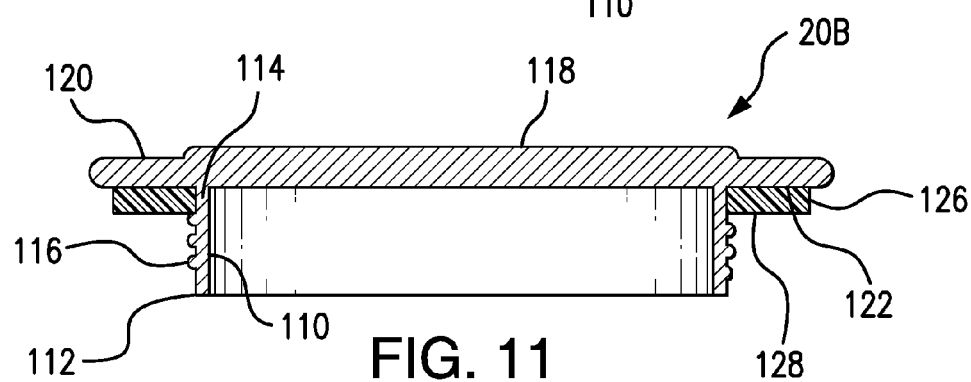
FIG. 11 shows a sectional view of the cap of FIG. 10 as seen along line 11-11 in FIG. 10.

FIGS. 10 and 11 show another embodiment of a cap 20B for use in the ice bag 10 shown in FIG. 1. As shown, the cap 20B includes a hollow cylindrical portion 110 that extends from a first end 112 to a second end 114. One or more thread features 116 extend from the outer wall of the cylinder portion 110 to establish a set of external, male threads for the cap 20B. Cap 20B includes a generally flat cover 118 closing the hollow cylindrical portion 110 at the second end 114. An annular flange 120 that extends outwardly from the cover 118 at second end 114 of cylindrical portion 110 and establishes a substantially flat flange surface 122. As shown, flange 120 extends to a flange gear-shaped flange edge having alternating concave-convex edge contours to provide convex grip surfaces of which convex grip surface 124a-c have been labeled. Cylindrical portion 110, thread features 116, annular flange 120 and cover 118 can be made of a one-piece rigid material, for example, a molded rigid plastic.

FIGS. 10 and 11 further show that the cap 20B includes an overmold material 126 overlying the flat flange surface 122. For example, the overmold material may have a thickness on the flange surface 122 in the range of about 0.5 to 15 mm. As shown, the surface 128 of the overmold material 126 opposite the flange 120 is substantially flat. Typically, the overmold material is a thermoplastic elastomer that is molded onto the rigid plastic flange 120 using an overmolding process.

Figure 12:
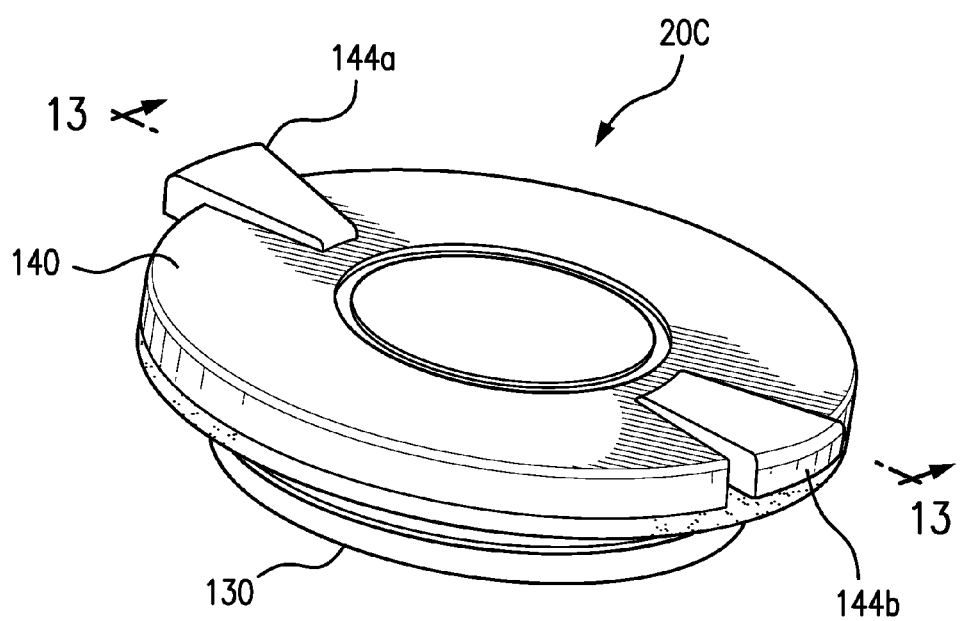
FIG. 12 shows a perspective view of another embodiment of a cap for use in the ice bag shown in FIG. 1.
Figure 13:
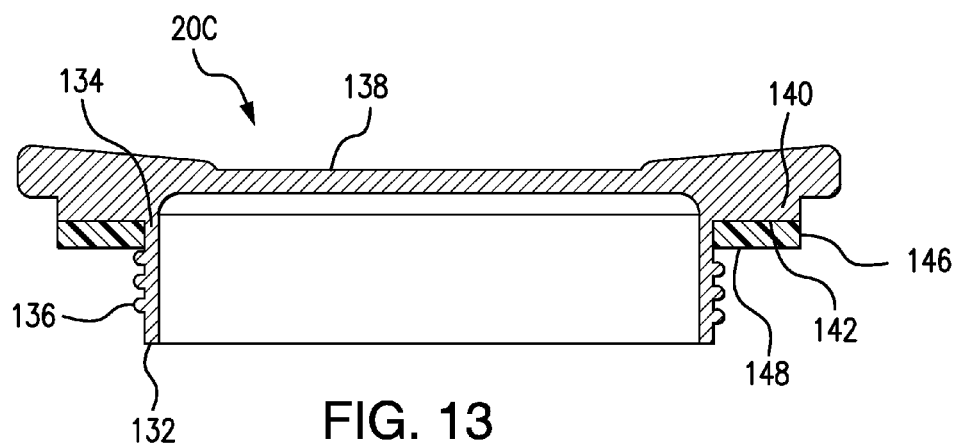
FIG. 13 shows a sectional view of the cap of FIG. 12 as seen along line 13-13 in FIG. 12.

FIGS. 12 and 13 show another embodiment of a cap 20C for use in the ice bag 10 shown in FIG. 1. As shown, the cap 20C includes a hollow cylindrical portion 130 that extends from a first end 132 to a second end 134. One or more thread features 136 extend from the outer wall of the cylinder portion 130 to establish a set of external, male threads for the cap 20C. Cap 20C includes a generally flat cover 138 closing the hollow cylindrical portion 130 at the second end 134. An annular flange 140 that extends outwardly from the cover 138 at second end 134 of cylindrical portion 130 and establishes a substantially flat flange surface 142. As shown, grips 144a,b extend from flange 140.

Cylindrical portion 130, thread features 136, annular flange 140, cover 138 and grips 144a,b can be made of a one-piece rigid material, for example, a molded rigid plastic.

FIGS. 12 and 13 further show that the cap 20C includes an overmold material 146 overlying the flat flange surface 142. As shown, the surface 148 of the overmold material 146 opposite the flange 140 is substantially flat. Typically, the overmold material is a thermoplastic elastomer that is molded onto the rigid plastic flange 140 using an overmolding process. For example, the overmold material may have a uniform thickness on the flange surface 142 in the range of about 0.5 to 15 mm.

Figure 14:
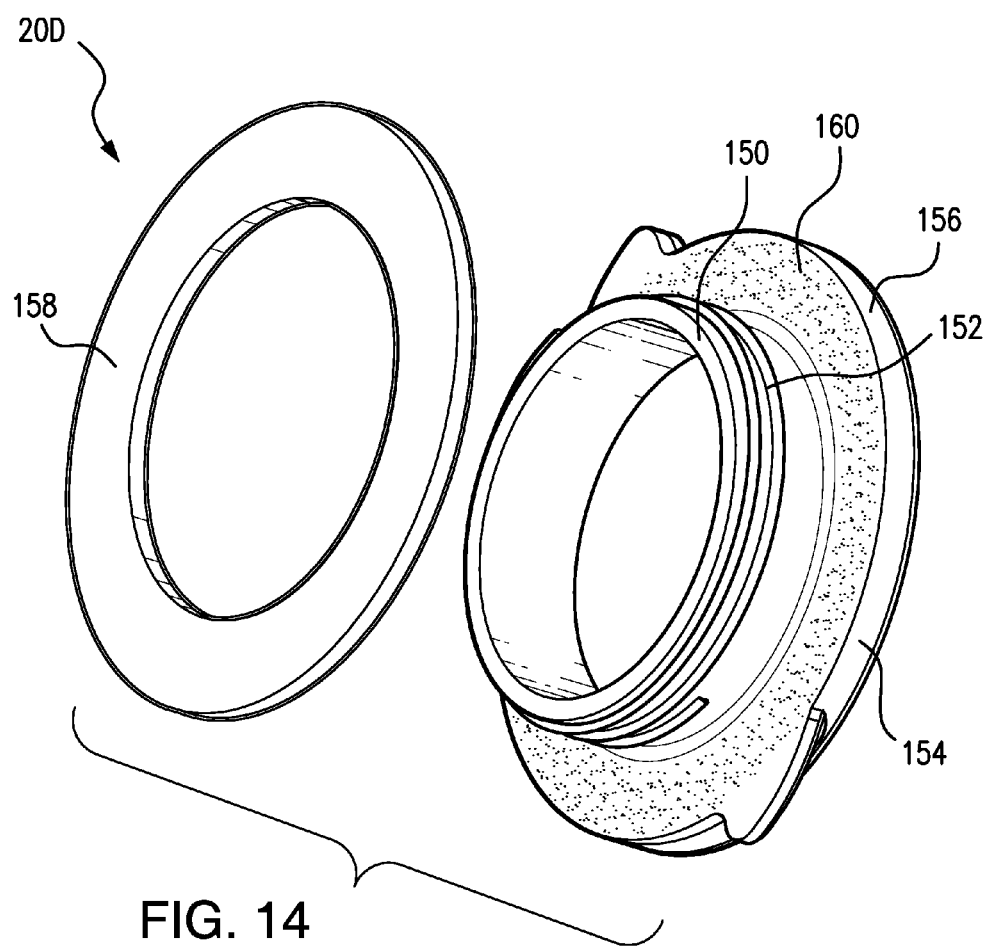
FIG. 14 shows an exploded, perspective view illustrating the assembly of another embodiment of a cap for use in the ice bag shown in FIG. 1.

FIG. 14 shows another embodiment of a cap 20D for use in the ice bag 10 shown in FIG. 1. As shown, the cap 20D includes a hollow cylindrical portion 150. One or more thread features 152 extend from the outer wall of the cylinder portion 150 to establish a set of external, male threads for the cap 20D. Cap 20D includes a generally flat cover closing the hollow cylindrical portion 150. An annular flange 154 extends outwardly from the cover and establishes a substantially flat flange surface 156. Cylindrical portion 150, thread features 152, annular flange 154 and cover can be made of a one-piece rigid material, for example, a molded rigid plastic. Alternatively, or in addition to including an overmold material overlying a flange surface of cap 20, 20A, 20B, 20C, 20D, 20E, 20F, 20G or 20H, an overmold material overlying a flange surface 32 of receiver 16 can be employed to provide a seal between the receiver 16 and cap 20, 20A, 20B, 20C, 20D, 20E, 20F, 20G or 20H.

FIG. 14 further illustrates that a ring shaped gasket 158 can be bonded to the flat flange surface 156 using an adhesive 160. Once bonded, the gasket 158 is affixed in place on the flange 154. Typically, the gasket 158 is made of an elastomer. Alternatively, or in addition to adhesively bonding a gasket to flange surface 156 of cap 20D, a gasket may be adhesively bonded to flange surface 32 of receiver 16 to provide a seal between the receiver 16 and cap 20D.

Cap 20, 20A 20B, 20C, 20D, 20E, 20F, 20G or 20H may be used with the receiver 16 shown or, alternatively, with a receiver that does not include an overmold material for coupling the receiver to a bladder (receiver not shown).

Figure 15:
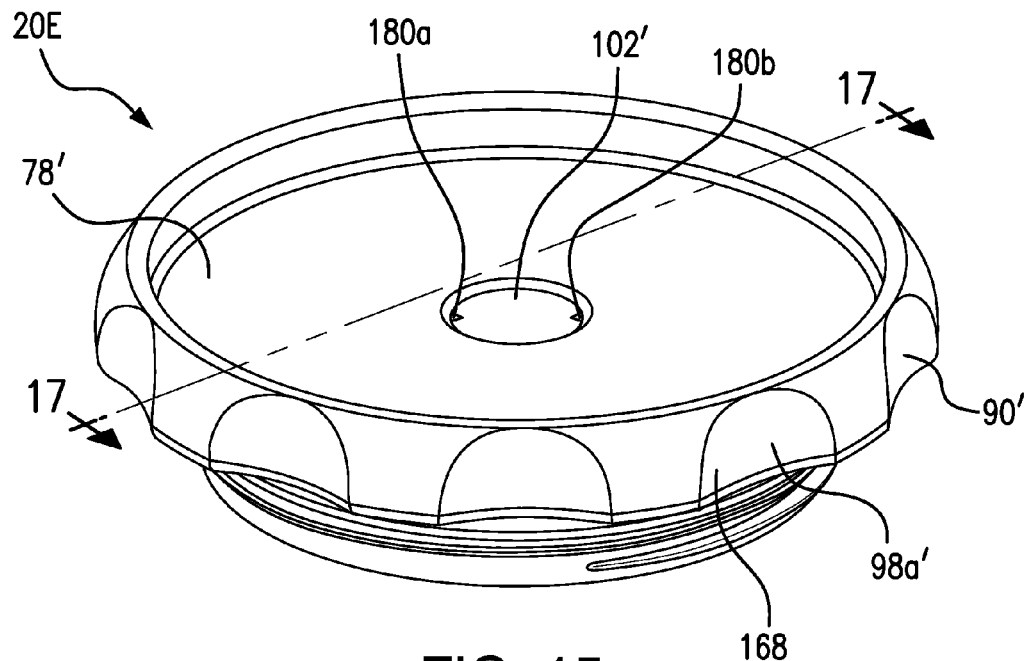
FIG. 15 shows a top perspective view of another embodiment of a cap for use in the ice bag shown in FIG. 1.
Figure 16:
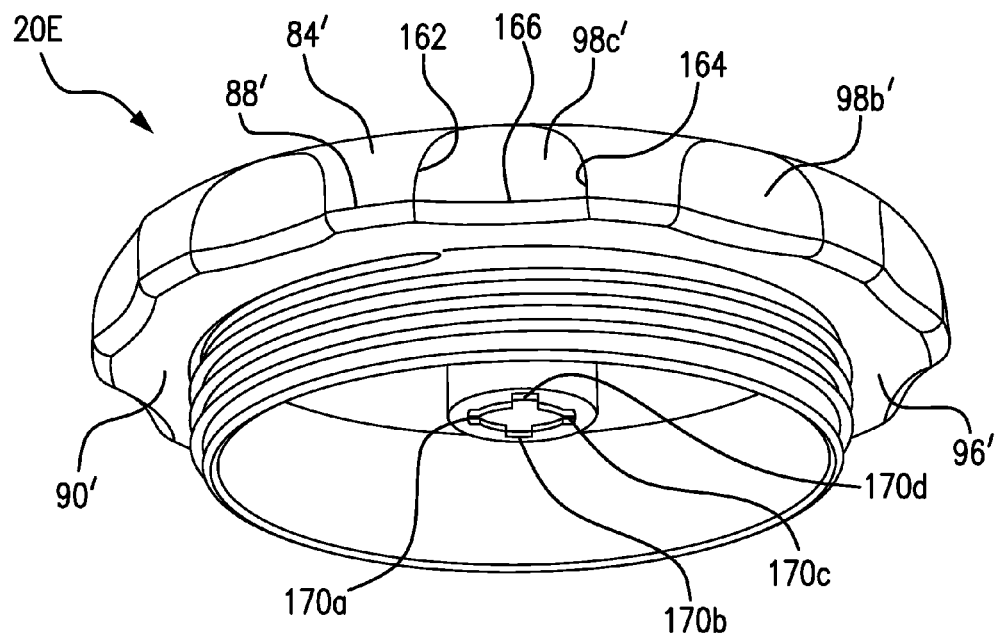
FIG. 16 shows a bottom perspective view of the cap shown in FIG. 15, shown with the valve stem removed to reveal the valve chamber openings.
Figure 17:
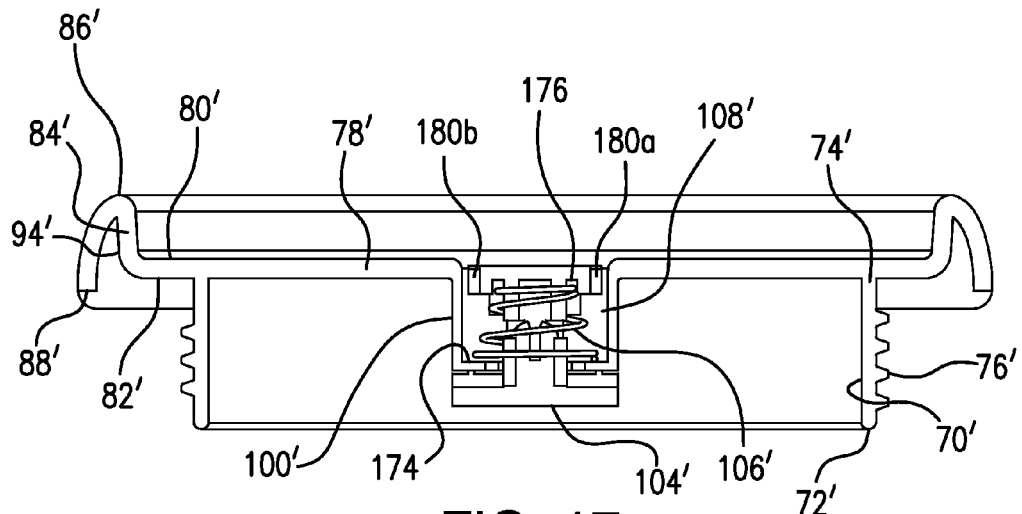
FIG. 17 shows a sectional view of the cap of FIG. 15 as seen along line 17-17 in FIG. 15 showing the valve in the closed position, shown with the grip/gasket overmold removed and the valve spring in perspective for clarity.
Figure 18:
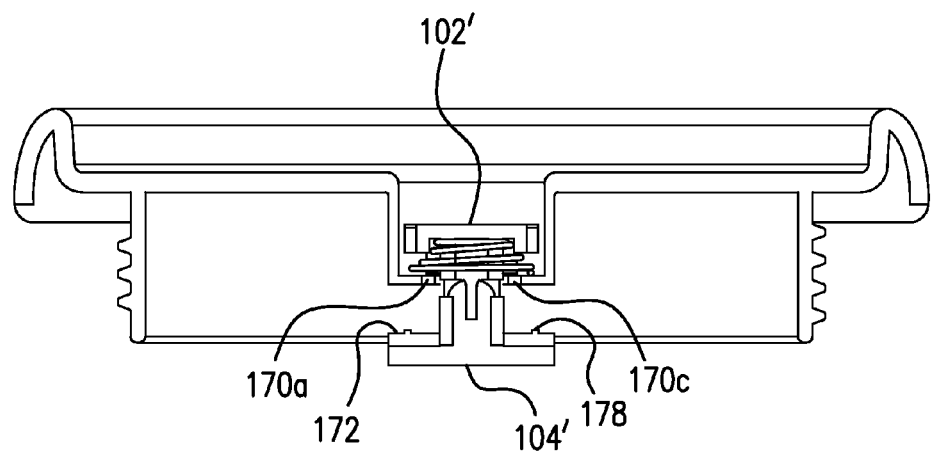
FIG. 18 shows a sectional view of the cap of FIG. 15 as seen along line 17-17 in FIG. 15 showing the valve in the open position, shown with the grip/gasket overmold removed and the valve spring in perspective for clarity.

FIGS. 15-18 show another embodiment of a cap 20E for use in the ice bag 10 shown in FIG. 1. As shown, the cap 20E includes a hollow cylindrical portion 70' that extends from a first end 72' to a second end 74'. One or more thread features 76' extend from the outer wall of the cylinder portion 70' to establish a set of external, male threads for the cap 20E. Cap 20E includes a generally flat cover 78' closing the hollow cylindrical portion 70' at the second end 74'. An annular flange 80' that extends outwardly from the cover 78' at second end 74' of cylindrical portion 70' and establishes a flange surface 82'. FIGS. 17 and 18 show that the flange 80' is substantially flat and extends away from the cover 78' to a lip 84'. As shown, lip 84' curls from the flange 80' through an apex 86' to an edge 88'. From the apex 86' to the edge 88', the lip 84' is formed with a plurality of cutouts that are spaced around the lip 84'. In some embodiments, the cutouts may be equally spaced around the lip 84'. Cylindrical portion 70', thread features 76', annular flange 80', lip 84' and cover 78' can be made of a one-piece rigid material, for example, a molded rigid plastic.

FIGS. 15 and 16 further show that the cap 20E includes an overmold material 90' overlying the flat flange surface 82' and inner surface 94' of curled lip 84'. As shown, the surface 96' of the overmold material 90' opposite the flange 80' is substantially flat. Typically, the overmold material is a thermoplastic elastomer that is molded onto the rigid plastic flange 80' and lip 84' using an overmolding process. For example, the overmold material may have a thickness on the flange 80' in the range of about 0.5 to 25 mm. FIGS. 15 and 16 show that the overmold material 90' extends to the edge 88' of the lip 84' to create a plurality of grips (of which grips 98a'-c' are labeled). As shown, the overmold material forms grips 98a'-c' that are flush with the surface of the lip 84' at grip edges 162, 164 and are indented between the edges 162, 164 to recess a midsection 166 at a radius slightly less than the radius of the lip edge 88. With this structure, each grip 98a' has a substantially concave surface 168, as shown.

FIGS. 15-18 also illustrate an embodiment of a valve 100' that may be incorporated into the cap 20E (or any of the other caps 20, 20A, 20B, 20C, 20D, 20F, 20G or 20H described herein). Alternatively, cap 20E may be configured without valve 100' in which case the cover 78' would be continuous like the cover 48 shown in FIG. 4. As shown in FIGS. 15-18, the valve 100' can include a button 102' that is manually depressible to release air from the bladder 12 (shown in FIG. 1) when the bladder is partially collapsed. As best seen in FIG. 17, the valve 100' includes a valve-stem 104' that is affixed to the button 102' and is biased in a closed position (shown closed in FIG. 17 and open in FIG. 18) by spring 106' to cover four openings 170a-d in chamber 108' with seal 172. As shown, spring 106' is compressed between a chamber end 174 and button flange 176. The button 102', valve stem 104' and chamber 108' are typically made of a rigid material. Seal 172 can be made of an overmold material, and can be formed with a raised ring 178 for establishing a tight seal with chamber end 174. Typically, the overmold material is a thermoplastic elastomer that is molded onto the rigid valve stem 104' using an overmolding process. Depressing button 102' moves stem 104' and seal 172 to uncover openings 170a-d (See FIG. 18). Air from the ice bag bladder (shown in FIG. 1) can then escape by flowing through the openings 170a-d, through the chamber 108' and out through holes 180a,b formed in button 102'.

The overmolded seal 172 provides a consistent, secure, air tight closure of the valve 100'. Because the overmolded seal 172 is integral with the valve stem 104' there are no small pieces that can become separated. The design of the valve 100' having more openings (e.g. four openings 170a-c at the valve inlet (i.e. bottom) of the valve 100' and fewer openings (e.g. two holes 180a,b on the button or valve outlet), allows an air pressure differential to be created within the valve chamber 108'. Note; the size of the openings 170a-c are substantially the same as the size of holes 180a,b. The air pressure differential creates a constant outwardly directed airstream when the valve is open and faster air release as compared to a valve having the same number of inlet holes and outlet holes.

Figure 19:
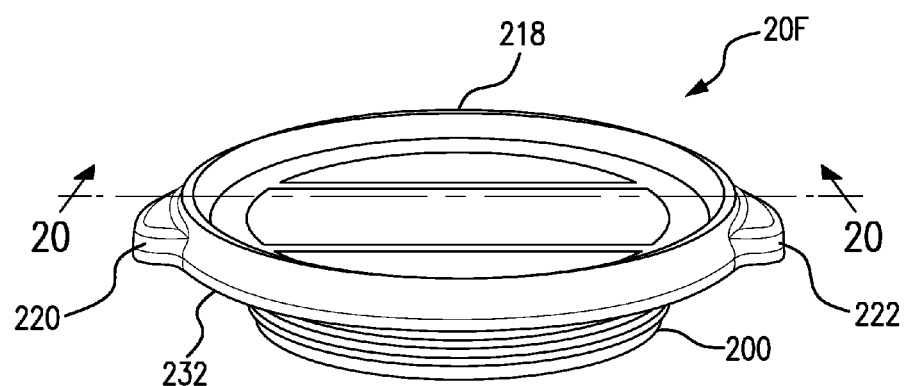
FIG. 19 shows a top perspective view of another embodiment of a cap for use in the ice bag shown in FIG. 1.
Figure 20:
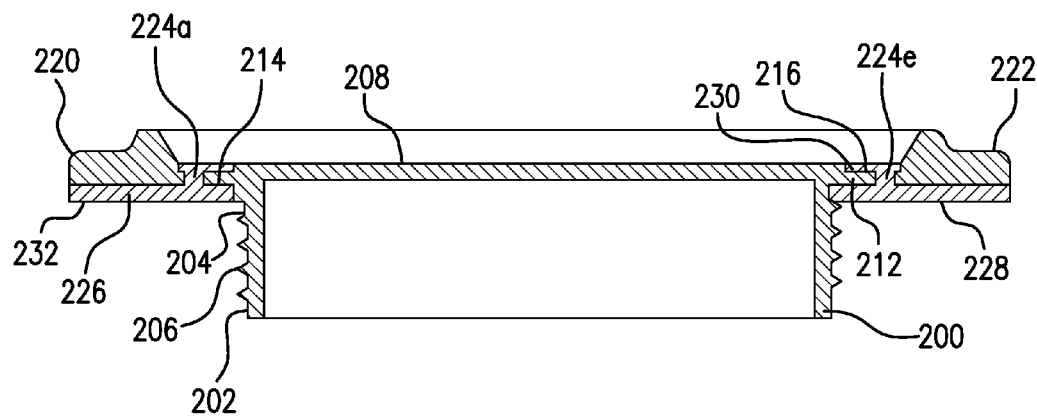
FIG. 20 shows a sectional view of the cap of FIG. 19 as seen along line 20-20 in FIG. 19.
Figure 21:
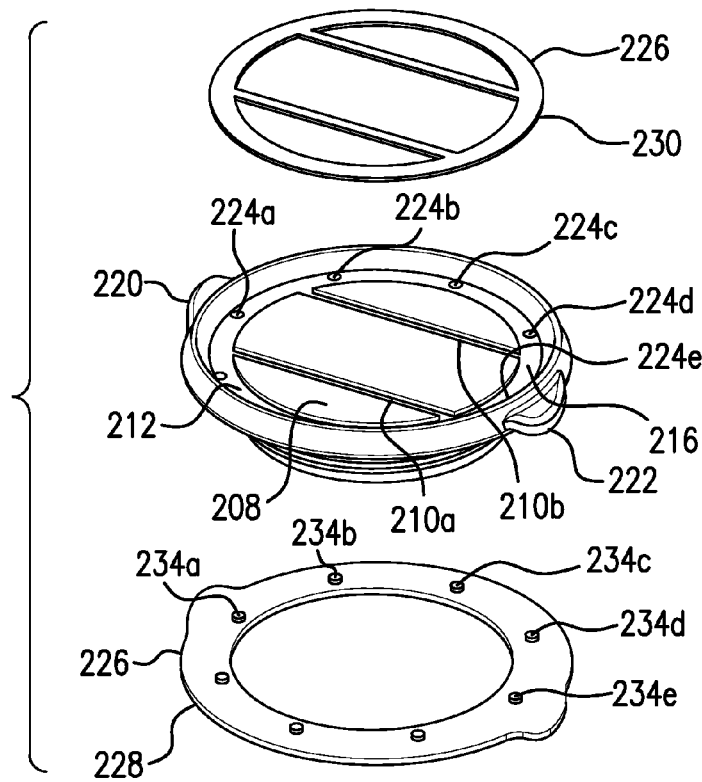
FIG. 21 shows a perspective view of the cap of FIG. 19, exploded to show the rigid portion and a continuous overmold portion having an overmold section which forms a seal on a first side of the rigid portion and an overmold section which forms a mechanical anchor for the seal on a second side of the rigid portion.

FIGS. 19-21 show another embodiment of a cap 20F for use in the ice bag 10 shown in FIG. 1. As shown, the cap 20F includes a hollow cylindrical portion 200 that extends from a first end 202 to a second end 204. One or more thread features 206 extend from the outer wall of the cylinder portion 200 to establish a set of external, male threads for the cap 20F. Cap 20F includes a generally flat cover 208 closing the hollow cylindrical portion 200 at the second end 204. Flat cover 208 is formed with recesses 210a,b on the surface opposite the cylinder portion 200. An annular flange 212 that extends outwardly from the cover 208 at second end 204 establishes flange surface 214 and opposed flange surface 216. It can be seen that flange surface 216 is recessed from the surface of the cover 208 (see FIG. 21). A raised annular portion 218 and a pair of grips 220, 222 extend from flange 212 to facilitate screwing the cap 20F into the receiver 16 (shown in FIG. 2). Cylindrical portion 200, thread features 206, annular flange 212, cover 208, raised annular portion 218 and grips 220, 222 can be made of a one-piece rigid material, for example, a molded rigid plastic.

Continuing with FIGS. 19-21, it can be seen that the flange 212 is formed with eight through-holes, of which through-holes 224a-e have been labeled. Although eight through-holes are shown for the cap 20F, it is to be appreciated that more than eight and as few as one though-hole may be used. It can further be seen that the cap 20F includes a continuous overmold material 226 which extends through each through-hole 224a-c, overlays the flange surface 216, and overlays the flange surface 218. Specifically, FIG. 21 shows the continuous, one piece overmold material 226 exploded into portion 228 and portion 230, for purposes of clarity. As shown, portion 228 overlays flange surface 214 and establishes a seal 232 for the cap 20F. Also shown, portion 230 overlays flange surface 216 and extends into recesses 210a and 210b of cover 208. Portion 228 is connected with portion 230 as a one piece, continuous overmold material by eight pegs, of which pegs 234a-e are labeled. The pegs 234a-e extend through the though-holes 224a-e, respectively, to connect overmold portion 228 with overmold portion 230. In this manner, the overmold portion 230 overlaying flange surface 216 forms a mechanical anchor for the seal 232. Should the overmolded seal 232 de-bond from the flange 212, the mechanical anchor (i.e. overmold portion 228) will keep the seal 232 in place against the flange 212. Typically, the overmold material 226 is a thermoplastic elastomer that is molded onto the rigid plastic flange 212 and grips 220, 222 using an overmolding process.

The installation of the cap 20F into the receiver 16 can best be appreciated by cross-referencing FIGS. 3, 19 and 20. To install, the first end 202 of the cap 20F is inserted in the second end 26 of the receiver 16 to engage thread portions 206 with thread portions 28. The cap 20F is then rotated relative to the receiver (using grips 220, 222) until the overmold seal 232 contacts the raised protrusion 36. Additional rotation of the cap 20F is then applied until the raised protrusion 36 compresses the overmold material seal 232 between the raised protrusion 36 and flange 212 to establish a water tight seal between the receiver 16 and cap 20F.

Figure 22:
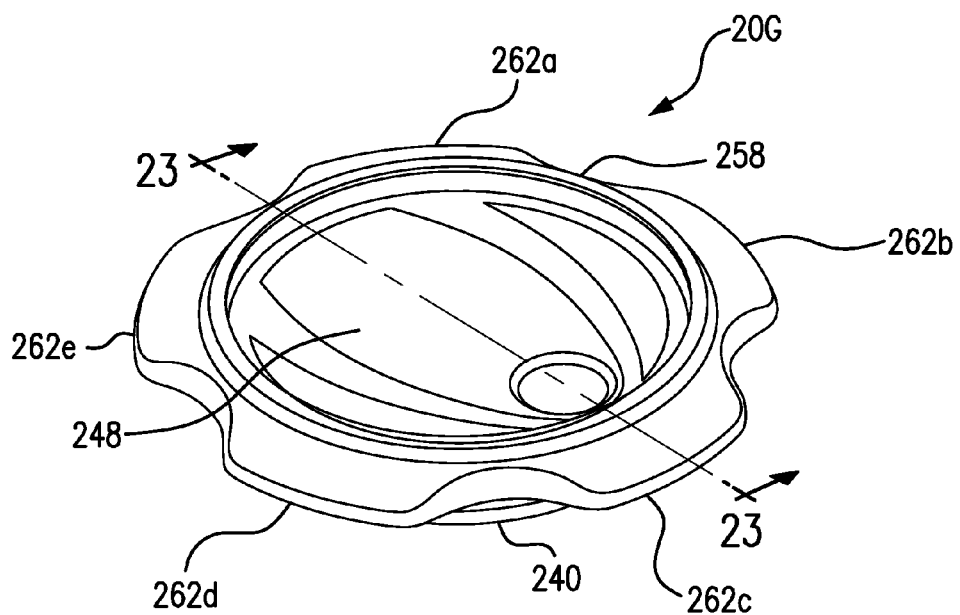
FIG. 22 shows a top perspective view of another embodiment of a cap for use in the ice bag shown in FIG. 1.
Figure 23:
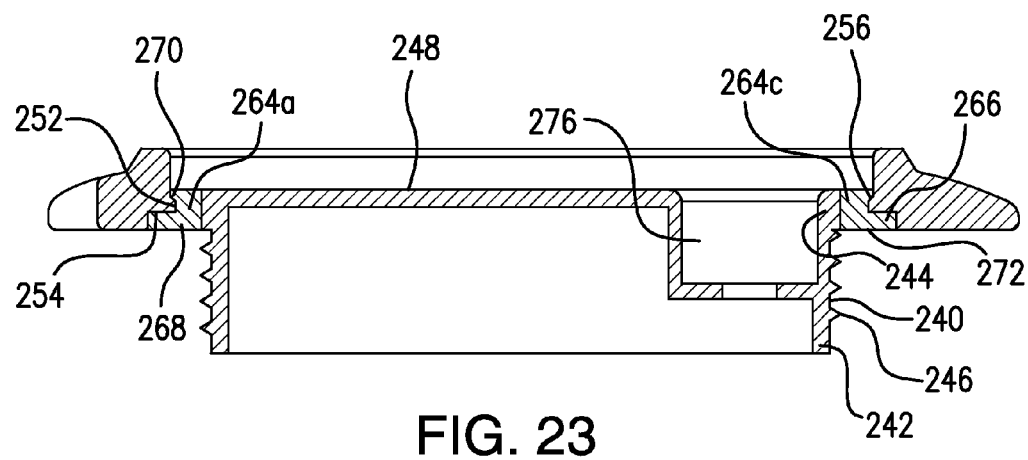
FIG. 23 shows a sectional view of the cap of FIG. 22 as seen along line 23-23 in FIG. 22 with valve components removed for clarity.
Figure 24:
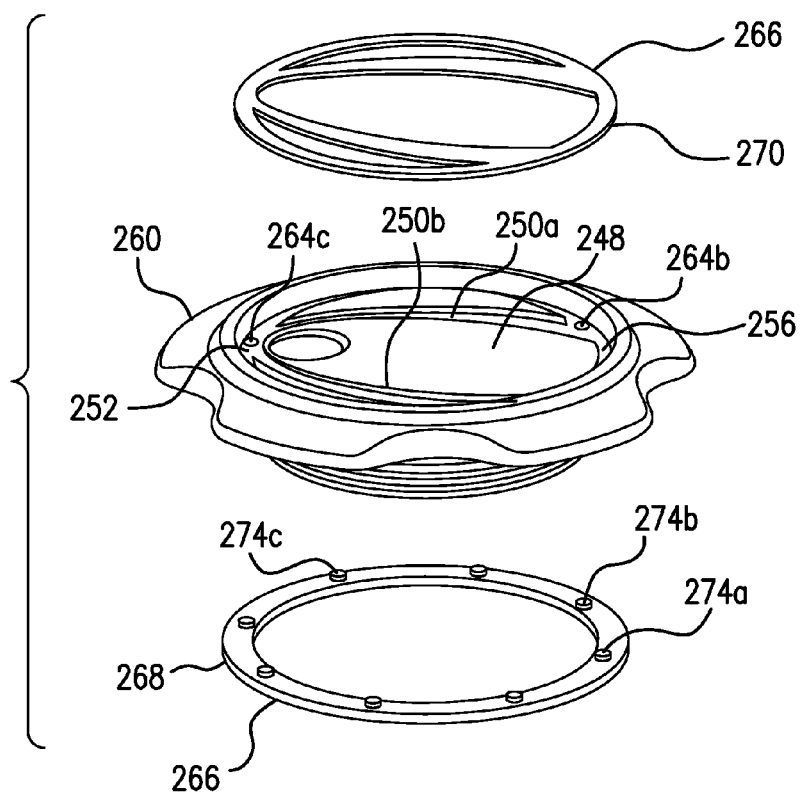
FIG. 24 shows a perspective view of the cap of FIG. 22, exploded to show the rigid portion and a continuous overmold portion having an overmold section which forms a seal on a first side of the rigid portion and an overmold section which forms a mechanical anchor for the seal on a second side of the rigid portion.

FIG. 22-24 show another embodiment of a cap 20G for use in the ice bag 10 shown in FIG. 1. As shown, the cap 20F includes a hollow cylindrical portion 240 that extends from a first end 242 to a second end 244. One or more thread features 246 extend from the outer wall of the cylinder portion 240 to establish a set of external, male threads for the cap 20G. Cap 20G includes a generally flat cover 248 closing the hollow cylindrical portion 240 at the second end 244. Flat cover 248 is formed with recesses 250a,b on the surface opposite the cylinder portion 240. An annular flange 252 that extends outwardly from the cover 248 at second end 244 establishes flange surface 254 and opposed flange surface 256. It can be seen that flange surface 256 is recessed from the surface of the cover 248 (see FIG. 24). A raised annular portion 258 extends from flange 252. Also, annular portion 260 extends from flange 252 and is formed with a plurality of indents to establish grips 262a-e to facilitate screwing the cap 20G into the receiver 16 (shown in FIG. 2). Cylindrical portion 240, thread features 246, annular flange 252, cover 248, raised annular portion 258 and annular portion 260 can be made of a one-piece rigid material, for example, a molded rigid plastic.

Continuing with FIGS. 22-24, it can be seen that the flange 252 is formed with eight through-holes, of which through-holes 264a-c have been labeled. Although eight through-holes are shown for the cap 20G, it is to be appreciated that more than eight and as few as one though-hole may be used. It can further be seen that the cap 20G includes a continuous overmold material 266 which extends through each through-hole 264a-c, overlays the flange surface 256, and overlays the flange surface 258. Specifically, FIG. 24 shows the continuous, one piece overmold material 266 exploded into portion 268 and portion 270, for purposes of clarity. As shown, portion 268 overlays flange surface 254 and establishes a seal 272 for the cap 20G. Also shown, portion 270 overlays flange surface 256 and extends into recesses 250a and 250b of cover 248. Portion 268 is connected with portion 270 as a one piece, continuous overmold material by eight pegs, of which pegs 274a-c are labeled. The pegs 274a-c extend through the though-holes 264a-c, respectively, to connect overmold portion 268 with overmold portion 270. In this manner, the overmold portion 270 overlaying flange surface 256 forms a mechanical anchor for the seal 272. Should the overmolded seal 272 de-bond from the flange 252, the mechanical anchor (i.e. overmold portion 268) will keep the seal 272 in place against the flange 252. Typically, the overmold material 266 is a thermoplastic elastomer that is molded onto the rigid plastic flange 252 and cover 248 using an overmolding process.

It can also be seen that the cover 248 forms a valve chamber 276. Valve components including a button, spring, valve stem and seal have been removed for clarity. These components, as described above and shown in FIGS. 17 and 18, can be used with the valve chamber 276 to establish a valve having a user operable button that is manually depressible to release air from the bladder 12 (shown in FIG. 1) when the bladder is partially collapsed.

The installation of the cap 20G into the receiver 16 can best be appreciated by cross-referencing FIGS. 3, 22 and 23. To install, the first end 242 of the cap 20G is inserted in the second end 26 of the receiver 16 to engage thread portions 246 with thread portions 28. The cap 20G is then rotated relative to the receiver (using grips 262a-e) until the overmold seal 272 contacts the raised protrusion 36. Additional rotation of the cap 20G is then applied until the raised protrusion 36 compresses the overmold material seal 272 between the raised protrusion 36 and flange 252 to establish a water tight seal between the receiver 16 and cap 20G.

Figure 25:
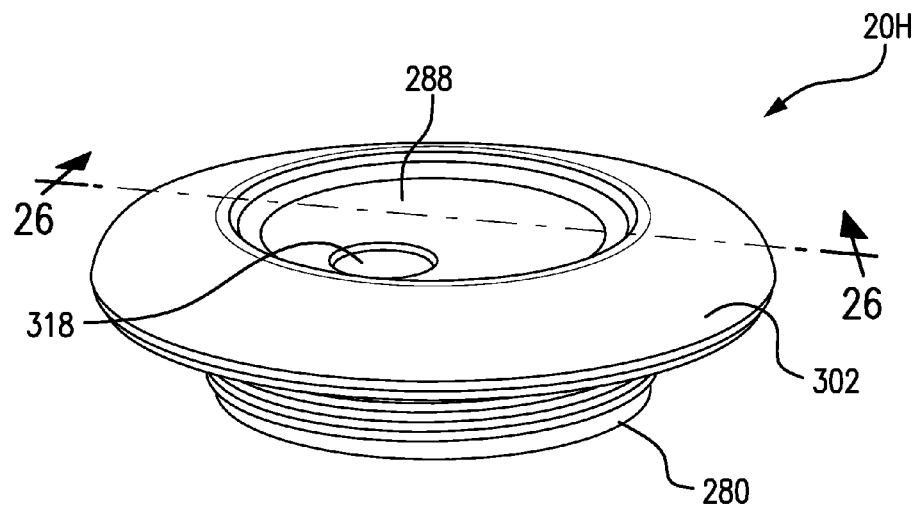
FIG. 25 shows a top perspective view of another embodiment of a cap for use in the ice bag shown in FIG. 1.
Figure 26:
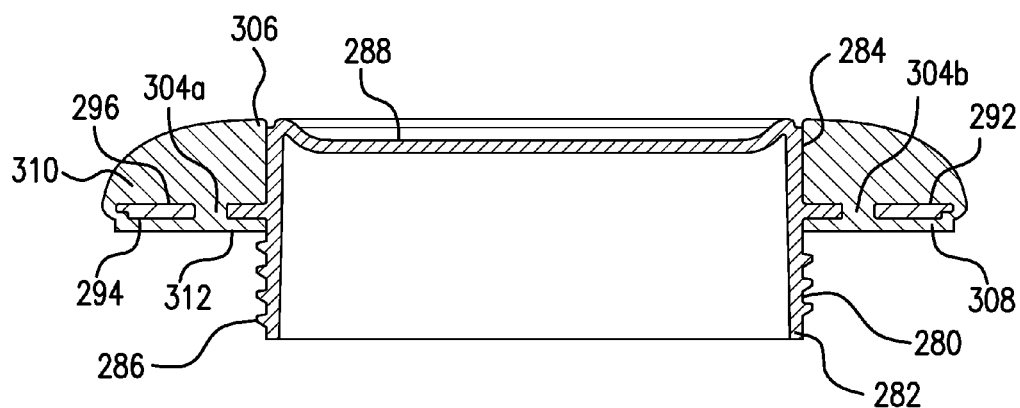
FIG. 26 shows a sectional view of the cap of FIG. 25 as seen along line 26-26 in FIG. 25.
Figure 27:
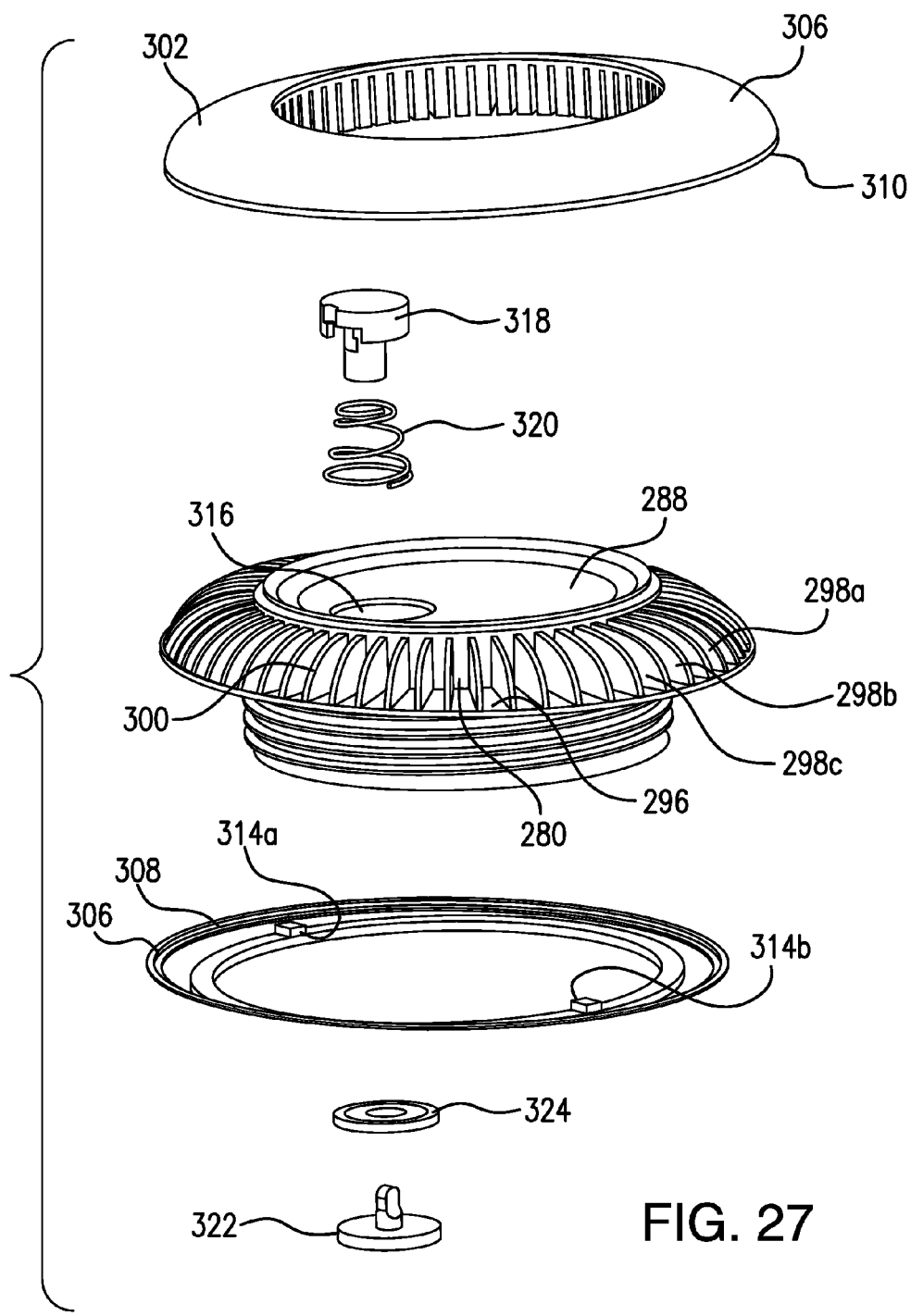
FIG. 27 shows a perspective view of the cap of FIG. 25, exploded to show the rigid portion and a continuous overmold portion having an overmold section which forms a seal on a first side of the rigid portion and an overmold section which forms a mechanical anchor for the seal on a second side of the rigid portion.

FIG. 25-27 show another embodiment of a cap 20H for use in the ice bag 10 shown in FIG. 1. As shown, the cap 20H includes a hollow cylindrical portion 280 that extends from a first end 282 to a second end 284. One or more thread features 286 extend from the outer wall of the cylinder portion 280 to establish a set of external, male threads for the cap 20H. Cap 20H includes a generally flat cover 288 closing the hollow cylindrical portion 280 at the second end 284. Flat cover 288 is slightly recessed into the cylindrical portion 280 from second end 284, as shown. An annular flange 292 that extends outwardly from the cylinder portion 280 at a distance from the second end 284 establishes flange surface 294 and opposed flange surface 296. A plurality of spaced apart ribs, of which ribs 298a-c are labeled, are arranged around the cylinder portion 280 with each rib 298a-c extending from flange surface 296 to the outer surface of the cylinder portion 280. Each rib 298a-c has a curved, somewhat circular outer edge 300 between the flange surface 296 to the outer surface of the cylinder portion 280. Cylindrical portion 280, thread features 286, cover 288, flange 292 and ribs 298a-c can be made of a one-piece rigid material, for example, a molded rigid plastic.

Continuing with FIGS. 25-27, it can be seen that the flange 292 is formed with two through-holes 304a,b. Although two through-holes are shown for the cap 20H, it is to be appreciated that more than two and as few as one though-hole may be used. It can further be seen that the cap 20H includes a continuous overmold material 306 which extends through each through-hole 304a,b, overlays the flange surface 296, and overlays the flange surface 298. Specifically, FIG. 27 shows the continuous, one piece overmold material 306 exploded into portion 308 and portion 310, for purposes of clarity. As shown, portion 308 overlays flange surface 294 and establishes a seal 312 for the cap 20H. Also shown, portion 310 overlays flange surface 296, extends between each pair of adjacent ribs 298a-c, and extends past the outer edge 300 of each rib 298a-c to establish a grip surface 302 for the cap 20H. Portion 308 is connected with portion 310 as a one piece, continuous overmold material by two pegs 314a,b. The pegs 314a,b extend through the though-holes 304a-c, respectively, to connect overmold portion 308 with overmold portion 310. In this manner, the overmold portion 310 overlaying flange surface 296 forms a mechanical anchor for the seal 312. Should the overmolded seal 312 de-bond from the flange 292, the mechanical anchor (i.e. overmold portion 308) will keep the seal 312 in place against the flange 292. Typically, the overmold material 306 is a thermoplastic elastomer that is molded onto the rigid plastic flange 292, ribs 298a-c and the outer surface of the cylindrical portion 280 using an overmolding process.

It can also be seen that the cover 288 forms a valve chamber 316. Valve components including a button 318, spring 320, valve stem 322 and seal 324 are shown in FIG. 27. These components, cooperate, as described above and shown in FIGS. 17 and 18 within the valve chamber 316 to establish a valve having a user operable button 318 that is manually depressible to release air from the bladder 12 (shown in FIG. 1) when the bladder is partially collapsed.

The installation of the cap 20H into the receiver 16 can best be appreciated by cross-referencing FIGS. 3, 25 and 26. To install, the first end 282 of the cap 20H is inserted in the second end 26 of the receiver 16 to engage thread portions 286 with thread portions 28. The cap 20H is then rotated relative to the receiver until the overmold seal 312 contacts the raised protrusion 36. Additional rotation of the cap 20H is then applied until the raised protrusion 36 compresses the overmold material seal 312 between the raised protrusion 36 and flange 292 to establish a water tight seal between the receiver 16 and cap 20H.

While the particular embodiment(s) are described and illustrated in this patent application in the detail required to satisfy 35 U.S.C. 112, it is to be understood by those skilled in the art that the above-described embodiment(s) are merely examples of the subject matter which is broadly contemplated by the present application. Reference to an element in the following Claims in the singular, is not intended to mean, nor shall it mean in interpreting such Claim element "one and only one" unless explicitly so stated, but rather "one or more". All structural and functional equivalents to any of the elements of the above-described embodiment(s) that are known, or later come to be known to those of ordinary skill in the art, are expressly incorporated herein by reference and are intended to be encompassed by the present Claims. It is not intended or necessary for a device or method discussed in the Specification as an embodiment, to address or solve each and every problem discussed in this Application, for it to be encompassed by the present Claims. No element, component, or method step in the present disclosure is intended to be dedicated to the public regardless of whether the element, component, or method step is explicitly recited in the Claims. No claim element in the appended Claims is to be construed under the provisions of 35 U.S.C. 112, sixth paragraph, unless the element is expressly recited using the phrase "means for" or, in the case of a method claim, the element is recited as a "step" instead of an "act".

What is claimed is:

1. A cap comprising;
a first portion formed of a rigid material, said first portion having a hollow cylindrical portion with an outer cylindrical surface having threads formed on a portion of the outer cylindrical surface, a flange having a first side and an opposed second side, the flange extending outwardly from the outer cylindrical surface, and at least two ribs, each rib having a curved surface extending from a location on the second side of the flange to a location on the outer cylindrical surface, the first portion formed with a through-hole in said flange; and
a second portion formed of an overmold material, the second portion extending through the though-hole and establishing a seal on the first side of the flange and overlying a surface of the second side of the flange with the second portion extending between the ribs to establish a mechanical anchor for the seal.

2. A cap as recited in claim 1 wherein each said rib extends from the flange to a curved outer edge.

3. A cap as recited in claim 2 wherein said overmold material extends from the flange and past the outer edge of each rib to establish a grip surface for the cap.

4. A cap as recited in claim 1 wherein said first portion is formed with a plurality of through-holes.

5. A cap as recited in claim 1 wherein said overmold material is a thermoplastic elastomer.

6. A cap as recited in claim 1 wherein said rigid material is a plastic.

7. A threaded cap for covering an opening of a container and providing a seal between the cap and the container, the threaded cap comprising;
a rigid portion having a threaded cylinder with a cover overlaying a first cylinder end and a flange having a first side and a second side, the flange extending from the threaded cylinder, the flange formed with a through-hole, the flange second side and cover establishing a first surface having raised portions and recessed portions; and
an elastomeric portion extending through the though-hole and overlaying the recessed portions of the first surface to establish an anchor for the seal having an annular portion and at least one connecting portion, the connecting portion extending from a first location on the annular portion to a second location on the annular portion and overlying at least a portion of the first side of the flange.

8. A threaded cap as recited in claim 7 wherein said elastomeric portion is made of a thermoplastic elastomer.

9. A threaded cap as recited in claim 7 wherein said elastomeric portion is made of an overmold material.

10. A threaded cap as recited in claim 7 wherein said flange is formed with a plurality of through-holes.

11. A threaded cap as recited in claim 7 wherein said rigid portion is made of a plastic.

12. A threaded cap as recited in claim 7 wherein said container is an ice bag.

13. A threaded cap as recited in claim 7 wherein the elastomeric portion overlaying at least a portion of the flange first side establishes the seal.

14. A threaded cap as recited in claim 7 wherein the connecting portion is a first connecting portion and the elastomeric portion overlaying the recessed portions of the first surface has a second connecting portion, extending from a third location on the annular portion to a fourth location on the annular portion.

15. A method for producing a cap comprising the steps of;
molding a first threaded component formed of a rigid material, said first component having a hollow cylindrical portion with an outer cylindrical surface having threads formed on a portion of the outer cylindrical surface, a flange having a first side and an opposed second side, the flange extending outwardly from the outer cylindrical surface, and at least two ribs, each rib having a curved surface extending from a location on the second side of the flange to a location on the outer cylindrical surface, the first threaded component formed with a through-hole in said flange; and
overmolding a thermoplastic elastomer material on the first threaded component, the thermoplastic elastomer material extending through the though-hole and establishing a seal on the first side of the flange and overlying a surface of the second side of the flange with the second portion extending between the ribs to establish a mechanical anchor for the seal.

16. The method as recited in claim 15 wherein said overmolding step is accomplished using a multi-shot injection molding process.

17. The method as recited in claim 15 wherein said overmolding step is accomplished using an insert molding processes.

18. The method as recited in claim 15 wherein the first threaded component is formed with a plurality of through-holes.

* * * * *